(12) United States Patent
Peters

(10) Patent No.: US 8,705,036 B2
(45) Date of Patent: Apr. 22, 2014

(54) METHOD AND DEVICE FOR DETERMINING THE STATIC AND/OR DYNAMIC SCATTERING OF LIGHT

(75) Inventor: Rainer Peters, Langen/Hessen (DE)

(73) Assignee: ALV-Laser Vertriebsgesellschaft mbH, Langen (DE)

( * ) Notice: Subject to any disclaimer, the term of this patent is extended or adjusted under 35 U.S.C. 154(b) by 0 days.

(21) Appl. No.: 13/520,819

(22) PCT Filed: Nov. 16, 2010

(86) PCT No.: PCT/EP2010/067533
§ 371 (c)(1),
(2), (4) Date: Jul. 26, 2012

(87) PCT Pub. No.: WO2011/088914
PCT Pub. Date: Jul. 28, 2011

(65) Prior Publication Data
US 2012/0281215 A1   Nov. 8, 2012

(30) Foreign Application Priority Data

Jan. 21, 2010   (DE) .................. 10 2010 005 962

(51) Int. Cl.
*G01N 21/55*   (2006.01)
(52) U.S. Cl.
USPC ........................... 356/434; 356/337; 356/338
(58) Field of Classification Search
USPC .......... 356/355–343, 417, 35–343; 250/458.1
See application file for complete search history.

(56) References Cited

U.S. PATENT DOCUMENTS

| | | | |
|---|---|---|---|
| 4,710,642 A | 12/1987 | McNeil | |
| 5,011,286 A * | 4/1991 | Petralli | 356/343 |
| 5,257,087 A * | 10/1993 | Furuya | 356/336 |
| 5,408,314 A * | 4/1995 | Perry et al. | 356/301 |
| 5,427,920 A * | 6/1995 | Berndt et al. | 435/34 |
| 5,760,900 A * | 6/1998 | Ito et al. | 356/338 |
| 5,956,139 A * | 9/1999 | Meyer et al. | 356/338 |
| 6,118,532 A | 9/2000 | Peters | |
| 6,459,093 B1 | 10/2002 | Dieckmann | |
| 6,714,299 B2 * | 3/2004 | Peterson et al. | 356/338 |
| 6,833,918 B2 * | 12/2004 | Kurozumi et al. | 356/336 |
| 7,268,874 B2 * | 9/2007 | Brogioli et al. | 356/336 |
| 7,916,293 B2 * | 3/2011 | Mitchell et al. | 356/336 |
| 2002/0030815 A1 * | 3/2002 | Ichijo | 356/339 |
| 2007/0146703 A1 * | 6/2007 | Adams et al. | 356/337 |
| 2007/0177149 A1 * | 8/2007 | Aronkyto et al. | 356/417 |

* cited by examiner

*Primary Examiner* — Sang Nguyen
(74) *Attorney, Agent, or Firm* — Andrew Wilford

(57) ABSTRACT

The invention relates to a method and device for determining the static and/or dynamic scattering of light. In the method, a plurality of different zones within a sample vessel (6) is illuminated during various time periods, wherein light is scattered on the sample. The scattered light is detected by means of a plurality of detectors (11, 12, 13, 14), wherein during the implementation of the method each detector captures scattered light from a plurality of different zones, and during a time period each detector detects scattered light from one zone and generates a signal. Said signals are transmitted to an electronic evaluation unit and are processed by said unit, wherein in each case those signals which are generated by the same detector and result from the detection of scattered light from the same zone are processed together.

10 Claims, 5 Drawing Sheets

METHOD AND DEVICE FOR DETERMINING THE STATIC AND/OR DYNAMIC SCATTERING OF LIGHT

CROSS REFERENCE TO RELATED APPLICATIONS

This application is the US-national stage of PCT application PCT/EP2010/067533 filed 16 Nov. 2010, published 28 Jul. 2010 as WO2011/088914, and claiming the priority of German patent application 102010005962.5 itself filed 21 Jan. 2010, whose entire disclosures are herewith incorporated by reference.

The present invention relates to a method of and an apparatus for evaluating static and/or dynamic light scattering. In this method several different zones within a sample container are illuminated during various periods of time, during which light is scattered on the sample. The scattered light is detected by a plurality of sensors, wherein each sensor detects scattered light from several different zones by performing the method, and each sensor detects scattered light from one zone during a period of time and generates a signal. These signals are transmitted to an electronic evaluation unit that processes the signals such that the signals generated by the same director and resulting from detection of scattered light from the same zone are processed together.

Measurement of the dynamic and/or static light scattering makes it possible to evaluate the particle size, the particle shape, the diffusion coefficients and the molecular weights of dissolved substances, for example. A light source emitting a coherent light and a sensitive single photon sensor are used to measure the average light intensity over time (static light scattering) and the time-dependent change in the light intensity (dynamic light scattering, DLS) of a sample in a solution. Any change in the scattering angle and thus the wave vector of the scattered light provides additional information in investigations of both static and dynamic light scattering. The total intensity of the scattered light measured in static-light scattering is higher, the larger the basic illuminated sample volume, after taking into account a few sample parameters, such as the sample concentration and the intensity of the incident light. In dynamic light scattering, the changes in light intensity of the coherent scattered light emitted by the sample at a certain point in time are compared (i.e. correlated) with the scattered light emitted by the same sample at a different point in time. Small test volumes or, alternatively, the use of any liquid volumes and coherent light are needed to ensure that mixing of the scattered light yields the most coherent possible light. However, incoherent or low-coherent mixing of the scattered light would illuminate the resulting change in the light intensity (usually due to diffusion of scattering centers in the solution), making it extremely difficult or even impossible to perform any further analysis.

DLS measurements are normally performed using single photon sensors such as photomultipliers (PMTS) or avalanche photodiodes (APDs) because the need for strictly coherent detection together with the usually small scattering cross section of the sample to be investigated allows only a very low detectable light intensity (typically in the range of less than 1 pW). Single photon counters are indispensable according to the current state of the art to be able to detect this low light intensity with the bandwidths that occur in the change in the light intensity (into the MHZ range). In most cases, a laser is used as the light source, and the measurement cell is at the center of the arrangement where usually a cylindrical glass or quartz glass cell is used to be able to detect the light scattering at any angles. Goniometers are traditionally used for such measurements, a laser unit being located on a stationary arm and the sensor being mounted on a pivotable arm. This apparatus is adjusted so that the sample is exactly at the center of rotation of a turntable with a rotating arm. The laser light is also directed at the sample at the center of rotation. This ensures that the same scattering volume is investigated in the entire range of scattering angles as long as the required adjustment is precise in all axes. In the case of instruments that perform measurements at a fixed angle, a more compact arrangement is possible because even simple cube-shaped cells with very small volumes can be used.

Different methods may be used for the data processing. To analyze the dynamic characteristic variables of the scattering centers (usually particles but also higher molecular molecules in general such as polymers or proteins), an autocorrelation of the measured signal over a certain period of time is performed. This data processing is taken over by an electronic signal evaluation unit (correlator) that supplies a so-called correlation function from which the average diffusion coefficient (or its distribution) of the scattering sensors can then be calculated and used to then calculate additional parameters such as the hydrodynamic radius. One sensor is normally used per scattering angle and transmits the measured signal to a correlator.

One important goal in optimizing DLS is to increase the accuracy of the measurement within a predetermined measurement time. However, this is limited by the fact that the random motion of the scattering centers (Brownian molecular motion) and coherent imaging due to light scattering of this random Brownian motion ultimately cause a rapid average change time, resulting from the diffusion coefficient and the scattering vector, as the change in the scattering intensity over time. This average change time defines the average number of such change cycles per unit of time and thus naturally also defines the average achievable accuracy of the measurement of this parameter. The resulting change in light intensity, which is relatively independent of the number of particles in question, remains constant because it is caused only by the coherent mixing of the scattering of all the scattering centers in question, so the changing portion of the scattered light remains constant relative to the total light scattered, regardless of the number of scattering centers in question, so increasing the illuminated/observed sample volume will not lead to more accurate measurement results per se. Instead of that, the measurement result must be averaged over multiple measurement sites that are independent of one another.

This may be accomplished by multiple measurements in succession, for example, although that obviously does not allow any improvement in accuracy in comparison with a continuous measurement of the same length or by parallel measurement on different mutually independent partial volumes within the sample volume performed by mutually independent measurement instruments.

U.S. Pat. No. 4,710,642 describes an apparatus for measuring scattered light in which the measurement accuracy is increased. With a plurality of sensors the microstructure of a sample can be measured over a broad range of the spatial frequency. A row of sensors is arranged at a right angle to the plane of the incident laser beam and of a mirror-reflected beam to detect the light scattered backward and forward in the perpendicular plane. Two laser beams with different wavelengths may be used to detect the optical properties of a film and of the underlying substrate. EP 0 867 711 [U.S. Pat. No. 6,118,532] describes a measurement instrument for evaluating static and/or dynamic light scattering where a plurality of sensors is arranged side by side at any angular spacings on a turntable. The scattered light of the same sample volume is always measured by observing the sample at different scattering angles. However, because of the high cost of single photon sensors and the complexity of the installation, there are limits to these methods. Alternatively, there are so-called multisensors having 32 sensors combined in one housing, for example. However, these are also large and expensive instruments.

One alternative for permitting multiple detection in DLS is to use a laser light source in combination with CCD (charge-coupled device) sensors that additionally allow a local resolution of the signals. However, the great disadvantage here is the substantially lower speed of readout (<100 images/sec for CCDs with a sensitivity comparable to that of single photon sensors) in comparison with single photon sensors (in the ns range). However, the light sensitivity is drastically reduced for more rapidly readable CCDs so these are no longer suitable in general for use in DLS.

One problem with DLS is that it is only possible to analyze highly diluted samples in which light is scattered at only one scattering center before it strikes the single photon sensor. As the particle concentration increases, there is an increase in the probability of light being scattered at more than just one scattering center, resulting in a distortion of the measurement result because the resulting scattering vector for this multiple scattering may then deviate randomly from single scattering. The need for great dilution of the sample, in addition to the very low anticipated light intensity of the scattered light, results in the fact that this method is very sensitive to contaminants. To nevertheless permit measurements to be performed at high particle concentrations, essentially two cross correlation techniques have been established, in which multiple measurements are performed in the same sample volume and at the same scattering angles. This suppresses multiple scattering, i.e. decorrelates it; in other words, its effect is distributed as a uniform random noise over the entire correlation function, thereby preventing systematic distortion of the correlation function. In 3D cross correlation, two laser beams are directed at the sample at different incident angles and the scattered light is again measured by two sensors. In dual-color cross correlation however, two laser beams of different wavelengths are directed at the sample at the same angles and the scattered light is measured by two sensors. Both of these methods are based on the idea of correlating the results of scattered light from identical scattering vectors with one another, although only in such a manner that the scattered light originates from different spatial zones. In this case, only the scattered light portions from the intended scattering vector enter into the correlation. In these techniques, data processing is also performed by a single electronic signal evaluation unit. EP 1 022 549 [U.S. Pat. No. 6,459,093] has already disclosed a method based on dynamic light scattering, in which a sample volume is illuminated simultaneously with a plurality of discrete wavelengths and each of the wavelengths is detected at approximately the same scattering angle. By using this method, the signal noise can be removed with the help of cross correlation.

All the methods from the state of the art have in common their long measurement time so that, for example, when a plurality of parameters (such as dilution series) must be investigated, DLS measurements may extend over an entire day, in particular when distribution functions of the diffusion coefficient or of the hydrodynamic radius are to be calculated because high precision correlation function data are indispensable for this calculation. The personnel costs are kept within limits, because such measurements are usually performed with automated procedures, but maintaining a stable environment for the measurements is both complicated and expensive. First, there are problems when the system runs for a longer period of time. There may be variations in the intensity of the laser due to thermal and/or electrical fluctuations. With many laser systems, it is also impossible to ensure that the wavelength of the laser light source will remain absolutely constant over a period of several hours. Temperature fluctuations may have a drastic effect on the viscosity of the solvent and thus have a substantial influence on the diffusion rate. Furthermore, the sample must also remain stable over a longer period of time. Instability of a sample is often caused by aggregation or gelation, polymerization and/or crystallization.

The object of the present invention is thus to overcome the known disadvantages of the prior art and to achieve a measurement accuracy that is many times higher within the same measurement period in comparison with "single-sensor measurements." An instrument that has a compact and simple design and is not too expensive is to be presented here. In addition, a locally resolved measurement is to be enabled, so that certain processes (for example, crystallization processes) taking place within a sample can be tracked in time and space. Furthermore, a bandwidth of the measurement in the µs range should be made possible so that the DLS measurements are not subject to any limitations due to particle size, viscosity or defined scattering angle, such as the limitations encountered with the methods known from the prior art.

This object is achieved by a method of evaluating static and/or dynamic light scattering, comprising the following steps:

illuminating multiple different zones within a sample container during various periods of time during which light is scattered on the sample, evaluating scattered light with a plurality of sensors that each detect scattered light from multiple different zones while the method is being performed and where each sensor detects scattered light from one zone during one period of time and generates a signal, transmitting the signals to an electronic evaluation unit and processing the signals by the electronic evaluation unit such that the signals generated by the same sensor and resulting from the detection of scattered light from the same zone are processed together.

In this method, in contrast with the methods known from the prior art, different zones and thus also independent scattering volumes are illuminated one after the other during different periods of time. In this process, light is scattered on the sample and detected by a plurality of sensors. A sensor detects scattered light from several zones during the process but it does so sequentially. Thus during each period of time, only scattered light from one scattering volume is detected and multiple signals are generated thereby. These signals are then transmitted to an electronic evaluation unit where the signals originating from scattered light from the same scattering volume and detected by the same sensor are processed together. The measurement data for each scattering volume is then transmitted to a correlator that generates a correlation function for each scattering volume.

The method according to the invention thus allows multi-parallel measurements at identical scattering angles. To increase the measurement accuracy N independent experiments—and thus also N single photon sensors—are needed, so that separate scattering volumes must be analyzed. The advantage of single photon counters is their speed in measurement that is in the ns range. However, diffusion of the scattering centers takes place at a much slower rate, so that no significant changes in the intensity of the scattered light occur in the µs range because the position of the scattering centers relative to one another has hardly changed during this period of time. This condition is utilized by using each single photon sensor for detecting different zones within the sample container that correspond to different scattering volumes in space, these scattering volumes being cycled in the sub-μs range and illuminated as a function of time. A regular measurement time (of about 1 μs) is broken down into several intervals here so that multiple scattering volumes in space can be analyzed within one measurement period (time multiplexing). The information from the single photon sensor is sent to an independent correlator subunit for signal analysis in synchronization with the respective illumination.

The different illumination of independent scattering volumes that are visible for the single photon sensors can be achieved by using multiple optically parallel laser light source that are activated and deactivated with a time offset (multiplexed). Cycling of the individual laser light sources must take place very rapidly here so that rapid particle diffusions can also be detected without distortion. The cycling is preferably at less than 1 μs, so that measurements can be performed in the range in which no significant fluctuations in the scattered light intensity occur. Cycle times in the range of several MHZ can be implemented easily using laser diodes, but higher output than in continuous operation is also made possible in pulsed operation. Furthermore, as a rule, the higher operating current that is possible in pulsed operation also leads to an improved coherence of the laser diode. Synchronization of illumination and detection with time multiplexing is also easily implementable and is possible with a resolution of less than 10 ns.

With the help of this novel method, a plurality of measurements can be performed in parallel on different scattering volumes. The number of parallel measurements is determined by the number of lasers and/or the number of scattering volumes (M) and the number of single photon sensors (N) and may be up to M×N. A measurement using the method according to the invention thus corresponds to M×N independent measurement instruments and leads to results that can be compared M×N times faster. Thus M×N times more accurate measurements are implemented in the same period of time than is possible using a conventional single sensor setup.

As an alternative, it is also possible to perform a measurement on M×N scattering volumes in space. This is important when certain processes are to be tracked in a sample such as crystallization, aggregation or polymerization. This novel method thus also permits a spatial resolution within the sample to be measured. Furthermore, this method is no longer limited to a certain particle size, solvent viscosity or scattering angle, as is the case with CCD-based approaches, because MHZ bandwidths are achieved. Another advantage of the method according to the invention is that it is easier to detect outliers in a measurement series. For example, if dirt or dust particles are interfering with a measurement, they can be evaluated reliably and removed from the calculation because they usually occur only at distinct locations in the sample volume over time.

In a preferred embodiment of the invention, the number of different zones is at least two, preferably at least three and in particular at least four. Preferably here if coherent light is used for illumination of the different zones. The preferred light source is a laser because only laser light is capable of interference with a time offset and only laser light sources can generate the required high light density, as they are monochromatic and spatially coherent. Since the scattering factor depends on the wavelength of the incident light, it is preferable if laser light of the same wavelength is used for illuminating the different zones. It is also preferable if measurements can be performed at different scattering angles, so that all the sensors will detect scattered light with the same value of the scattering vector.

In another preferred embodiment of the method according to the invention, the number of sensors is at least two, preferably at least four and in particular at least 16. Alternatively it is preferable if the sensors are allocated to the same scattering angle.

The electronic evaluation unit preferably has multiple correlator subunits and allows simultaneous calculation of multiple correlation functions, such that signals are transmitted from one sensor to the same correlator subunit in each case for the correlation calculation. The signals generated by the same director and resulting from the detection of scattered light from the same zone are always processed together. Thus the information from one scattering volume is sent to one correlator so that a correlation function can be generated for each scattering volume.

In another preferred embodiment, the different zones are zones that are spatially separated from one another such that the spatial spacing of the zones is selected so that mutually independent nonoverlapping observation zones are obtained through the selected observation lens system. A typical illumination geometry used for DLS is a weakly focused diffraction limited laser beam having a radius of 150 μm (based on the $1/e^2$ intensity) at the focal point and an only very slightly divergent beam waist. For such an illumination geometry, an arrangement of the zones with a separation of 0.4 mm (center to center distance) from one another would be possible. The different zones are then mutually independent nonoverlapping scattering volumes such that the spatial geometry is variable. The zones may be designed to be both vertical and horizontal.

In another preferred embodiment of the method, the different zones are illuminated sequentially in a repeating periodic or random sequence in which the repeat period is less than 10 μs, preferably less than 2 μs and in particular less than 1 μs. In illumination of the different zones in a repeating periodic sequence, the different zones are each illuminated in the same sequence (for example in three zones: illumination of zones 1, 2, 3, 1, 2, 3, etc.). When talking of a repeating random sequence, this means that the illumination sequence changes with each illumination period (for example for three zones: illumination of zones 1, 3, 2, 3, 1, 2, etc.). In this way it is possible to reduce or even prevent systematic errors that might occur due to a purely periodic illumination.

An apparatus for evaluating static and/or dynamic light scattering is also a component of the present invention, comprising at least one sample container; a light source capable of illuminating different zones within the sample container during different periods of time; a plurality of sensors arranged in such a way that each sensor can detect light from several of the zones and an electronic evaluation unit that is connected to the sensors.

In a preferred embodiment of the apparatus according to the invention, it is designed so that
  the number of different zones amounts to at least two, preferably at least three and in particular at least four and/or
  the light source is a laser light source, where it is preferable for the light source to have multiple laser diodes, the number of laser diodes preferably being at least two, especially preferably at least three and in particular at least four and/or
  the light source having an optical and/or optoelectric device capable of separating the generated light into a plurality of beam bundles that can be switched on and off at separate times from one another, it being preferable if the number of beam bundles is at least two, preferably at least three and in particular at least four and/or the light source has a lens system capable of deflecting the generated light so that different zones within the sample container are illuminated during different periods of time.

In another advantageous embodiment, the number of sensors is at least two, preferably at least three, and in particular at least four, such that it is preferable if the sensors are arranged at the same scattering angle and/or if the sensors are single photon sensors.

In an advantageous embodiment, the electric evaluation unit has a plurality of correlator subunits for calculating the correlation functions so that an independent correlation function is calculated for the signals of each sensor for each illuminated zone such that the number of correlation subunits preferably amounts to at least two, especially preferably at least 48 and in particular at least M×N where M is the number of zones and N is the number of sensors.

In another advantageous embodiment, the sensors are connected to the electronic evaluation unit via a multiplexer. A multiplexer is a selection circuit that can select one of a plurality of input signals. With the help of a demultiplexer, the combined data channels can be separated again.

The invention will be explained in greater detail below with reference to drawings, the invention of course not being limited to the embodiments shown here. Therein:

Figure 1:
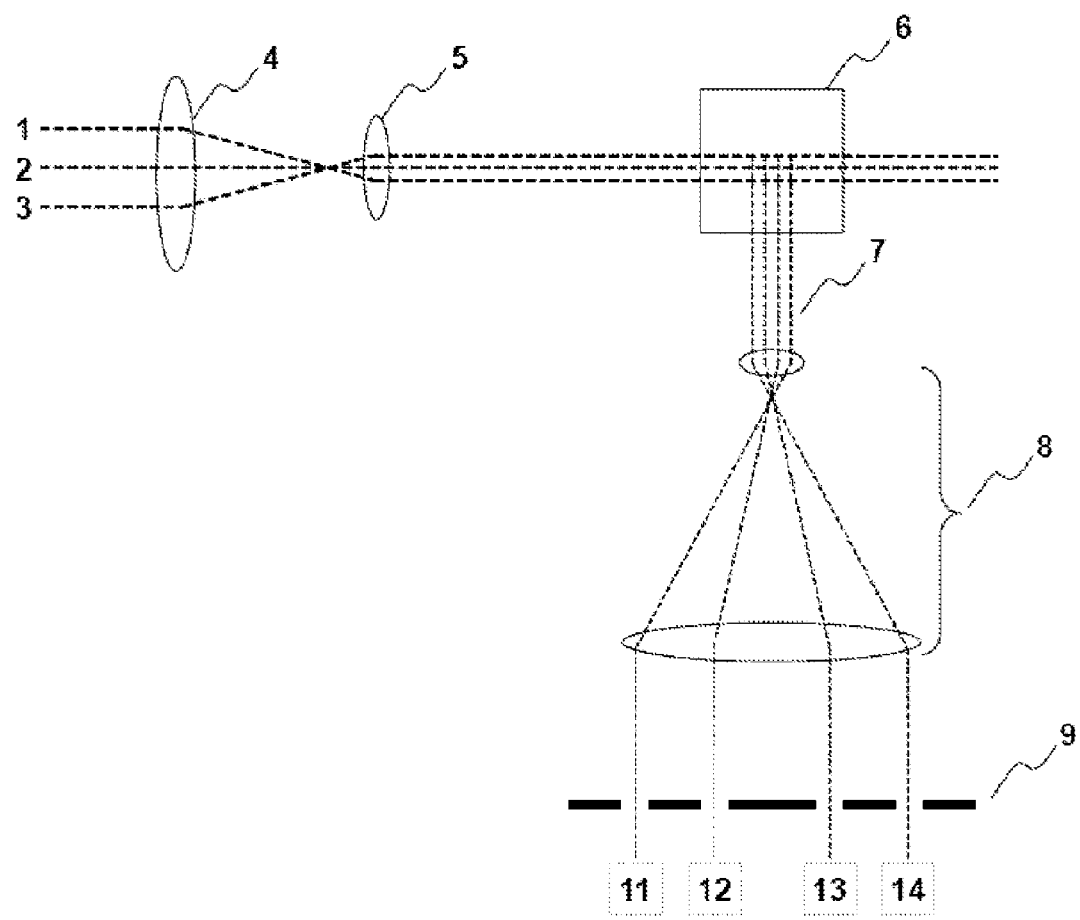
FIG. 1 is a schematic view of test setup for multiparallel measurements.

FIG. 1 shows schematically a test setup for multiparallel measurements. In this example, three lasers 1, 2, 3 are designed and set up in parallel to one another and are directed by a lens system 4, 5 in parallel into a sample container 6 with a slight lateral offset amounting to at most 1 mm. The individual or multidetection units with single photon sensors 11, 12, 13, 14 receive scattered light 7 from the sample in the sample container at a scattering angle of 90°. Mutually independent scattering volumes arranged close together are defined by a microscopic lens system 8 and aperture systems 9 and are enlarged optically so that such a zone in space illuminates only one single photon counter and/or one channel of a multiphoton counter. The cycling of the laser in this example amounts to 100 ns "on time" per laser every 300 ns.

Figure 2:
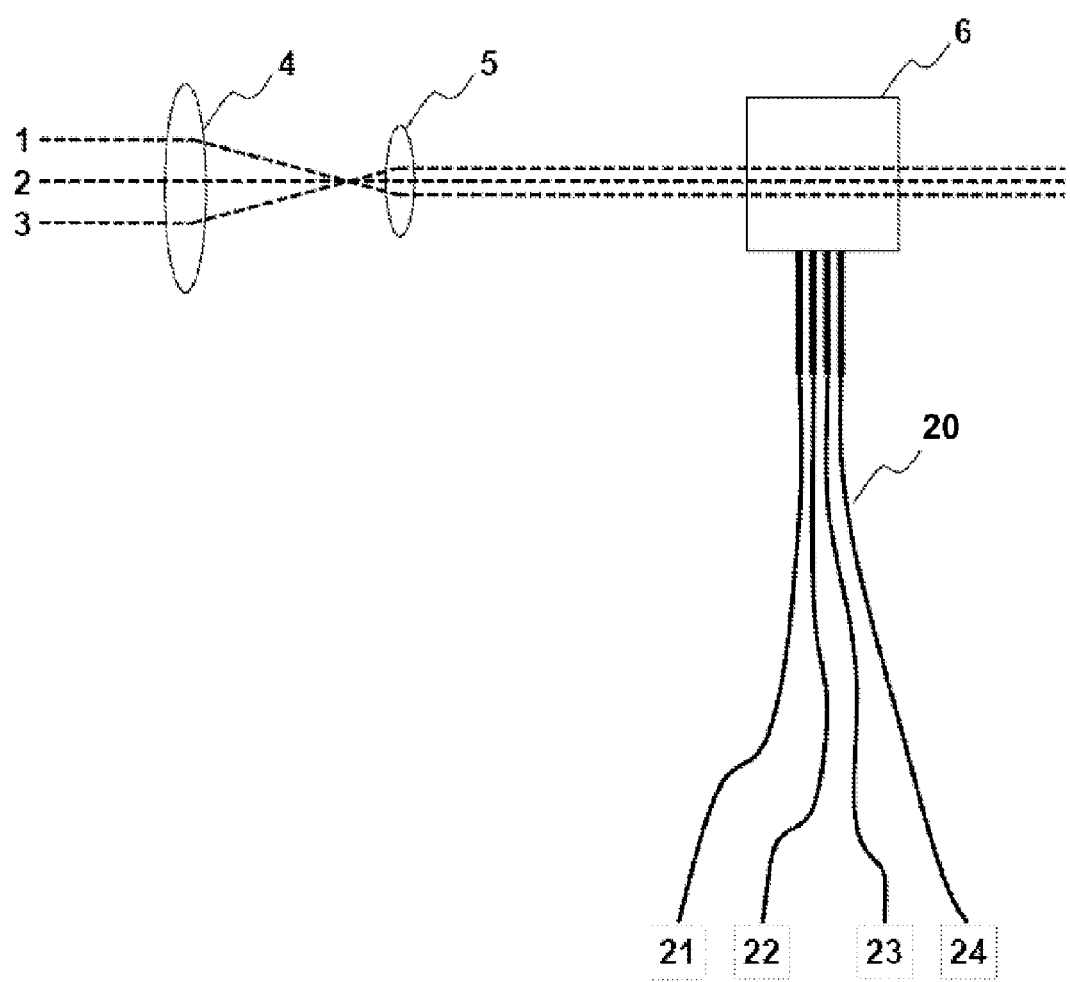
FIG. 2 shows the schematic test setup for multiparallel measurements using fiber optics and FIG. 3 shows in the FIGS. 3a through 3c the cycling of three lasers in the course of the method according to the invention.

FIG. 2 shows an alternative test setup. As an alternative to the microscope lens system with an aperture system, optical fibers 20 may also be used to feed the light to the individual sensors. Fiber sensors 21, 22, 23, 24 yield a higher light intensity with better coherence of the captured light in comparison with the traditional pinhole sensors because of their property of selecting only a few transverse modes from the total scattered light of a sample. Both multimode fibers and single mode fibers may be used. A parallel beam path is generated by a collimator and thus the detection of the parallel component of the scattered light alone is ensured.

Mixed designs having both elements from classical optics as well as fiber-optic components are also conceivable.

Figure 3:
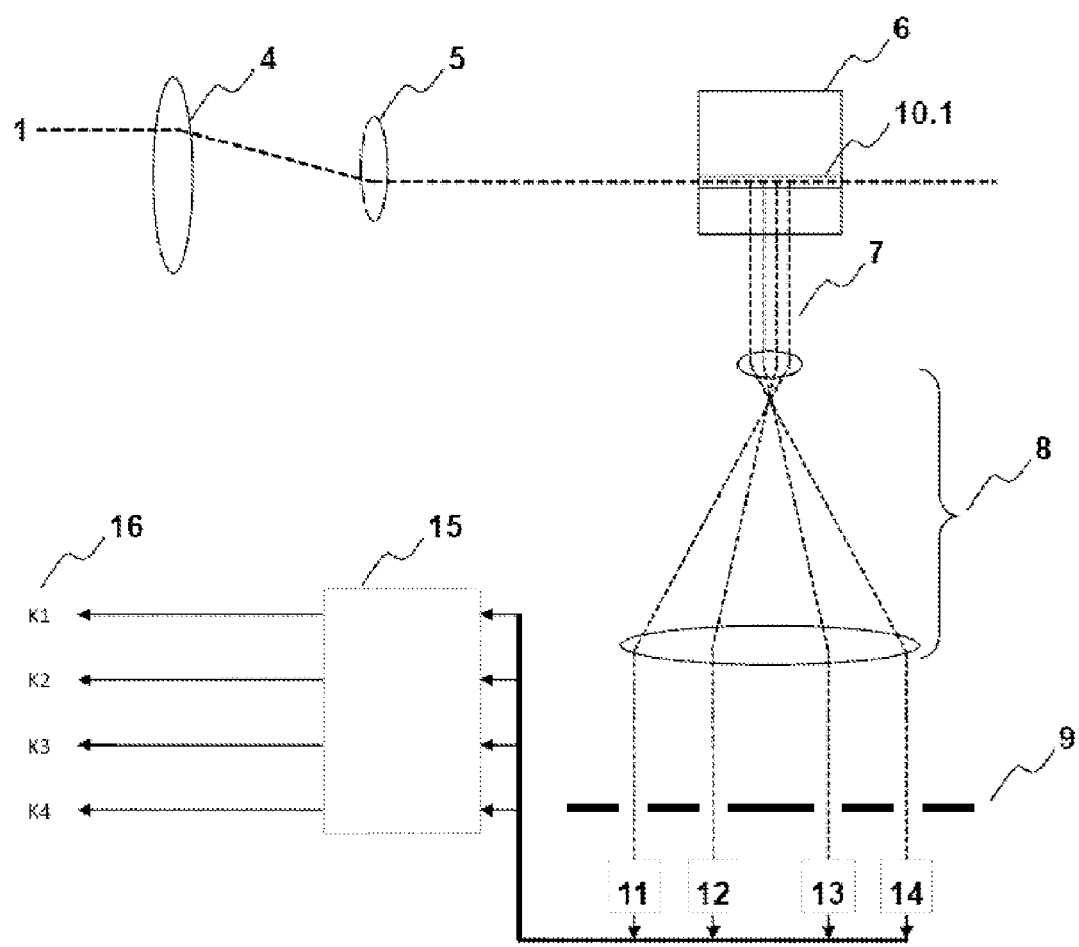
Figure 3:
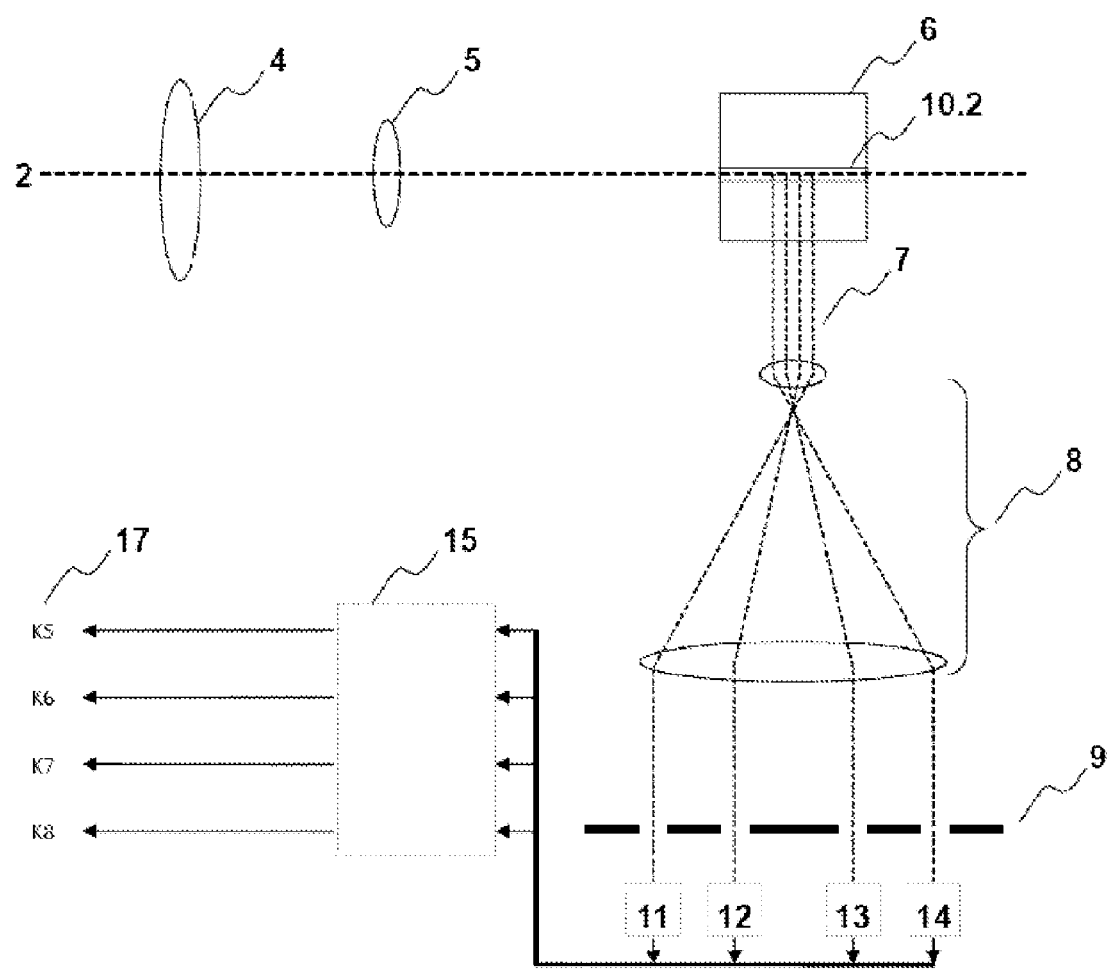
Figure 3:
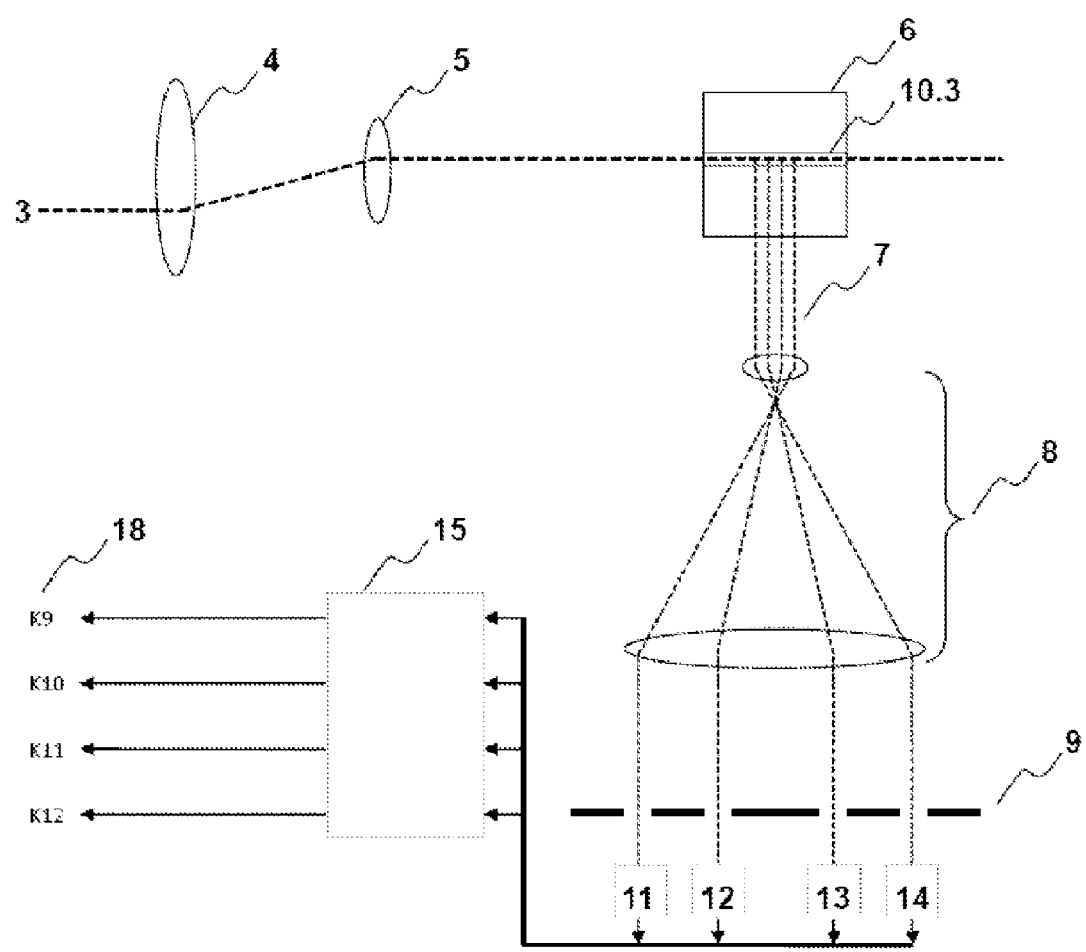

FIG. 3 shows in the individual FIGS. 3a through 3c the cycling of the individual lasers in the course of the method according to the invention at respective points in time t1, t2 and t3. The laser 1 is turned on at time t1 in FIG. 3a, so that a certain scatter volume 10.1 is illuminated. The light 7 scattered on the sample 6 thereby is transmitted to four single photon sensors 11, 12, 13, 14 that each generate a respective signal that is transmitted to a multiplexer 15. The signals are then processed by an electronic evaluation unit consisting of a plurality of correlator subunits 16, 17, 18, where the signals of each of the correlator subunits 1 through 4, which are generated by the same sensor and result from detection of scattered light from the same zone, are processed 16 together. When the next laser 2 is turned on at time t2, a different scattering volume 10.2 is illuminated. The light scattered on the sample 6 is again transmitted to the four single photon sensors 11, 12, 13, 14, each of which generates a signal that is transmitted to the multiplexer 15. The signals generated by the same sensor are then processed 17 by the correlator subunits 5 through 8. When the third laser 3 is turned at the time t3, another scattering volume 10.3 is illuminated and the signals generated by the sensors 11, 12, 13, 14 are processed 18 by the correlator subunits 9 to 12. In this example of a method, each scattering volume is illuminated for 100 ns, so that this process is repeated every 300 ns. In this case, it is possible to perform 12 parallel measurements in a period of 300 ns and thus one minute of measurement time corresponds to 12 minutes of measurement time on a conventional single sensor design. This allows measurements that are 12 times more accurate in the same period of time. With the method according to the invention it is quite realistic to use five laser diodes and 32 single photon sensors, achieving a factor of 160.

List of Reference Numerals

1 Laser beam 1
2 Laser beam 2
3 Laser beam 3
4 Focusing device
5 Lens
6 Sample
7 Scattered light
8 Microscope lens system
9 Aperture
10.1 Scattering volume 1
10.2 Scattering volume 2
10.3 Scattering volume 3
11 Single photon sensor 1
12 Single photon sensor 2
13 Single photon sensor 3
14 Single photon sensor 4
15 Multiplexer
16 Correlator subunits 1-4
17 Correlator subunits 5-8
18 Correlator subunits 9-12
20 Optical fibers
21 Fiber sensor 1
22 Fiber sensor 2
23 Fiber sensor 3
24 Fiber sensor 4

The invention claimed is:

1. A method of evaluating static and/or dynamic light scattering, the method comprising the steps of:
   illuminating within a sample container during various periods of time multiple different spatially separate zones each partitioned into a plurality of different subzones;
   selecting with a selected observation lens system a spacing of the zones so that mutually independent nonoverlapping observation zones each having a plurality of different subzones belonging to respective zones are obtained and light is scattered on the sample;
   detecting the scattered light with a plurality of sensors each assigned to a respective observation zone and detecting scattered light from multiple different subzones while the method is being performed and with each sensor detecting scattered light from one subzone during a period of time and generating a signal; and transmitting the signals to an electronic evaluation unit and processing the signals by the electronic evaluation unit with the signals generated by the same sensor and resulting from detection of scattered light from the same subzone and thus in the same period of time being processed together.

2. The method according to claim 1, wherein the number of different zones is at least two, coherent light being used for illuminating the different zones.

3. The method according to claim 1, wherein the number of sensors is at least two, the sensors preferably being arranged at the same scattering angle.

4. The method according to claim 1, wherein the electronic evaluation unit has a plurality of correlator subunits that simultaneously calculate a plurality of correlation functions, the signals being transmitted from the sensors to the same respective correlator subunits for the correlation calculation.

5. The method according to claim 1, wherein the different zones are illuminated successively in a repeating, periodic or random sequence having a repeat period of less than 10 µs.

6. An apparatus for evaluating static and/or dynamic light scattering, the apparatus comprising:

a sample container;

a light source for illuminating within the sample container during different periods of time different spatially separate zones each partitioned into a plurality of different subzones, a spacing of the zones being selected so that mutually independent nonoverlapping observation zones each having a plurality of subzones belonging to a plurality of different zones are obtained through the selected observation lens system;

a plurality of sensors arranged so that each sensor is assigned to a respective observation zone and detects scattered light from multiple different zones and each sensor detects scattered light from one zone during one period of time and generates a signal; and an electronic evaluation unit connected to the sensors for processing the signals with the signals generated by the same sensor and resulting from detection of scattered light from the same zone and thus in the same period of time being processed together for the correlation calculation.

7. The apparatus according to claim 6, wherein the number of different zones amounts to at least two, or the light source is a laser light source having at least two laser diodes, or the light source has an optical or optoelectric device capable of separating the generated light into at least two bundles that are switchable on and off at separate times from one another, or the light source has a lens system capable of deflecting the generated light so that different zones within the sample container are illuminated during different periods of time.

8. The apparatus according to claim 6, wherein the number of sensors is at least two, the sensors being arranged for detection in the same scattering angle or the sensors being single photon sensors.

9. The apparatus according to claim 6, wherein the electronic evaluation unit has at least two correlator subunits for calculation of the correlation function so that an independent correlation function is calculated for the signals of each sensor for each illuminated zone.

10. The apparatus according to claim 6, further comprising a multiplexer connecting the sensors to the electronic evaluation unit.

* * * * *